US010524944B1

(12) United States Patent
Burkart et al.

(10) Patent No.: US 10,524,944 B1
(45) Date of Patent: Jan. 7, 2020

(54) DELIVERY SYSTEMS AND METHODS OF ENDOLUMINAL DELIVERY OF BRANCHED VASCULAR ENDOPROSTHETIC DEVICES

(71) Applicant: W. L. Gore & Associates, Inc., Newark, DE (US)

(72) Inventors: Dustin C. Burkart, Bellemont, AZ (US); Mark Fillinger, Hanover, NH (US); Larry L. Gibbs, Flagstaff, AZ (US); Brandon C. Hedberg, Flagstaff, AZ (US); Jason D. Hemmer, Flagstaff, AZ (US); Timothy E. Johnston, Flagstaff, AZ (US); Levon M. Majure, Flagstaff, AZ (US); Steven W. Nelson, Flagstaff, AZ (US); Jonathan W. Thom, Flagstaff, AZ (US); Daniel J. Westphal, Flagstaff, AZ (US); William Wilkie, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 616 days.

(21) Appl. No.: 14/608,922

(22) Filed: Jan. 29, 2015

Related U.S. Application Data

(60) Provisional application No. 61/933,227, filed on Jan. 29, 2014.

(51) Int. Cl.
*A61F 2/954* (2013.01)
*A61F 2/966* (2013.01)
(Continued)

(52) U.S. Cl.
CPC ............ *A61F 2/954* (2013.01); *A61F 2/07* (2013.01); *A61F 2/966* (2013.01); *A61F 2002/065* (2013.01); *A61F 2250/001* (2013.01)

(58) Field of Classification Search
CPC .......... A61F 2/954; A61F 2/958; A61F 2/966; A61F 2/962; A61F 2/97; A61F 2/07;
(Continued)

(56) References Cited

U.S. PATENT DOCUMENTS 5,591,228 A 1/1997 Edoga
6,042,605 A 3/2000 Martin et al.
(Continued)

FOREIGN PATENT DOCUMENTS

AU 2013206712 B1 * 11/2013 ............... A61F 2/07
EP 2 606 851 6/2013
(Continued)

OTHER PUBLICATIONS

Bellandi G., Venturuzzo G. Endovascular Bilateral Evolutive Common Iliac Artery Aneurysm Repair Using a Zenith Branch Graft Through a Combined Femora-Brachial Approach in a Patient with Previous EVAR. Eur J Vasc Endovasc Surg (2910) 40; pp. 596-598.

*Primary Examiner* — Katherine H Schwiker

(57) ABSTRACT

A catheter assembly for delivery of an expandable implant having at least one branch portal, which utilizes a secondary sleeve for releasably constraining a middle portion of the expandable implant after releasing a primary constraining sleeve used for constraining the expandable implant toward a delivery configuration for endoluminal delivery; and methods of using the same.

41 Claims, 13 Drawing Sheets

(51) Int. Cl.
*A61F 2/07* (2013.01)
*A61F 2/06* (2013.01)

(58) Field of Classification Search
CPC ...... A61F 2/89; A61F 2/95; A61F 2002/9556; A61F 2002/075; A61F 2002/077; A61F 2002/065; A61F 2002/067; A61F 2002/072; A61F 2002/061; A61F 2002/9505; A61F 2002/9511; A61F 2/852; A61F 2/856; A61F 2002/826; A61F 2002/828; A61F 2002/821; A61F 2250/006; A91F 2002/9522; A91F 2002/9528; A91F 2002/9534; A91F 2002/9517

See application file for complete search history.

(56) References Cited

U.S. PATENT DOCUMENTS

| | | |
|---|---|---|
| 6,352,561 B1 | 3/2002 | Leopold et al. |
| 6,361,637 B2 | 3/2002 | Martin et al. |
| 6,379,319 B1 | 4/2002 | Garibotto et al. |
| 6,520,986 B2 | 2/2003 | Martin et al. |
| 6,645,242 B1 | 11/2003 | Quinn |
| 7,144,421 B2 | 12/2006 | Carpenter et al. |
| 8,273,115 B2 | 9/2012 | Hamer et al. |
| 8,663,306 B2 | 3/2014 | Kasprzak et al. |
| 2004/0117003 A1 | 6/2004 | Ouriel et al. |
| 2005/0182476 A1* | 8/2005 | Hartley .............. A61F 2/07 623/1.11 |
| 2007/0179590 A1 | 8/2007 | Lu et al. |
| 2008/0269866 A1* | 10/2008 | Hamer .............. A61F 2/07 623/1.11 |
| 2009/0259298 A1* | 10/2009 | Mayberry .............. A61F 2/07 623/1.35 |
| 2011/0087318 A1 | 4/2011 | Daugherty et al. |
| 2012/0109279 A1* | 5/2012 | Mayberry .............. A61F 2/07 623/1.11 |
| 2012/0232645 A1 | 9/2012 | Machold et al. |
| 2013/0046371 A1 | 2/2013 | Greenberg et al. |
| 2013/0289713 A1* | 10/2013 | Pearson .............. A61F 2/07 623/1.35 |
| 2014/0257453 A1* | 9/2014 | Roeder .............. A61F 2/954 623/1.11 |
| 2014/0277355 A1* | 9/2014 | Roeder .............. A61F 2/954 623/1.12 |

FOREIGN PATENT DOCUMENTS

| | | |
|---|---|---|
| WO | 2006/052322 | 5/2006 |
| WO | 2011/116308 | 9/2011 |

* cited by examiner

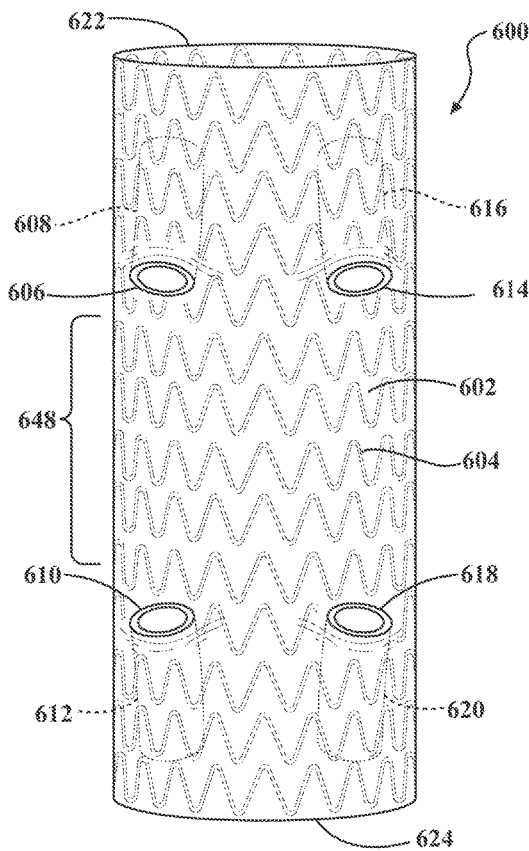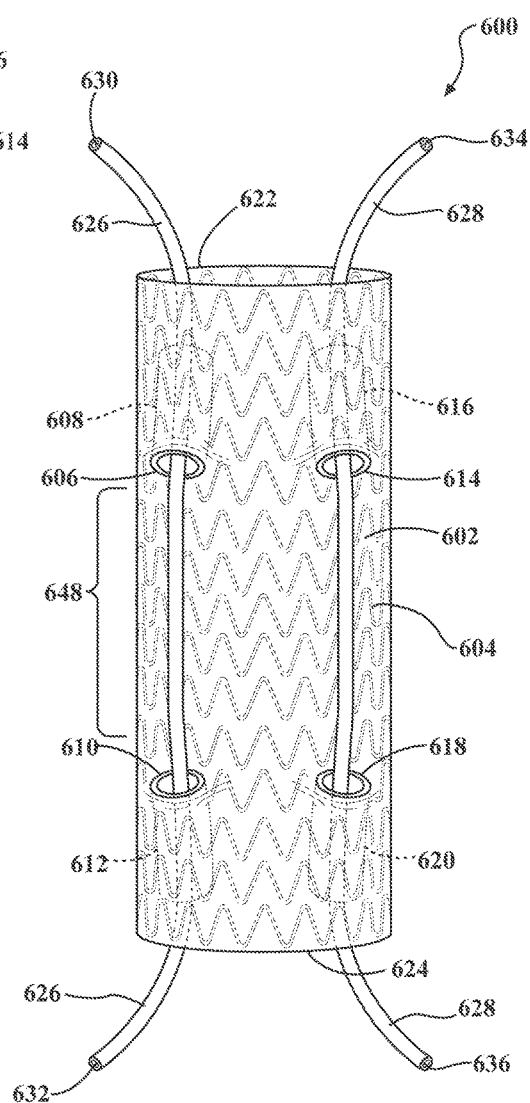
FIG. 6A
FIG. 6B

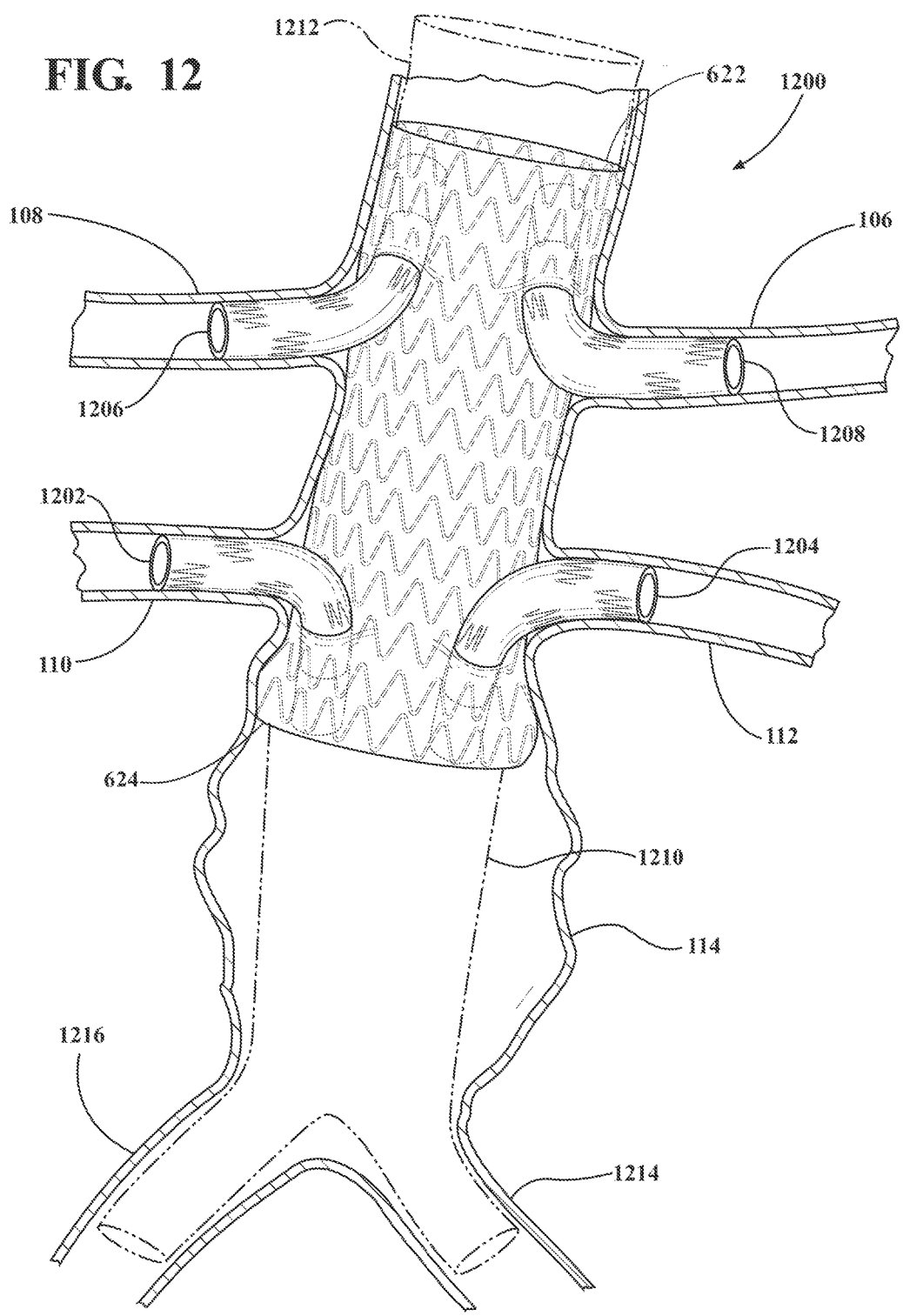

DELIVERY SYSTEMS AND METHODS OF ENDOLUMINAL DELIVERY OF BRANCHED VASCULAR ENDOPROSTHETIC DEVICES

FIELD

The present disclosure relates to delivery systems and methods of endoluminally delivering branched vascular endoprosthetic devices to vascular treatment sites.

BACKGROUND

There is a need for advanced devices, tools, systems and methods used for the endoluminal treatment of aortic diseases, particularly in the descending aorta adjacent to the celiac artery, superior mesenteric artery and the two renal arteries. Such devices and methods can require four branch vessels along with the capability to engage an optional distal bifurcated device and an optional proximal extender device.

BRIEF DESCRIPTION OF THE DRAWINGS

The features and advantages of the present disclosure will become more apparent from the detailed description set forth below when taken in conjunction with the drawings.

FIG. 6A is a perspective view of a stent graft having four side branch portals.

FIG. 6B is a perspective view of a stent graft having four side branch portals with two removable guidewire tubes placed through the four side branch portals.

FIG. 12 is the cross-sectional representation of a human anatomy with a fully expanded stent graft having four branch devices expanded into four branch vessels.

DETAILED DESCRIPTION

Figure 1:
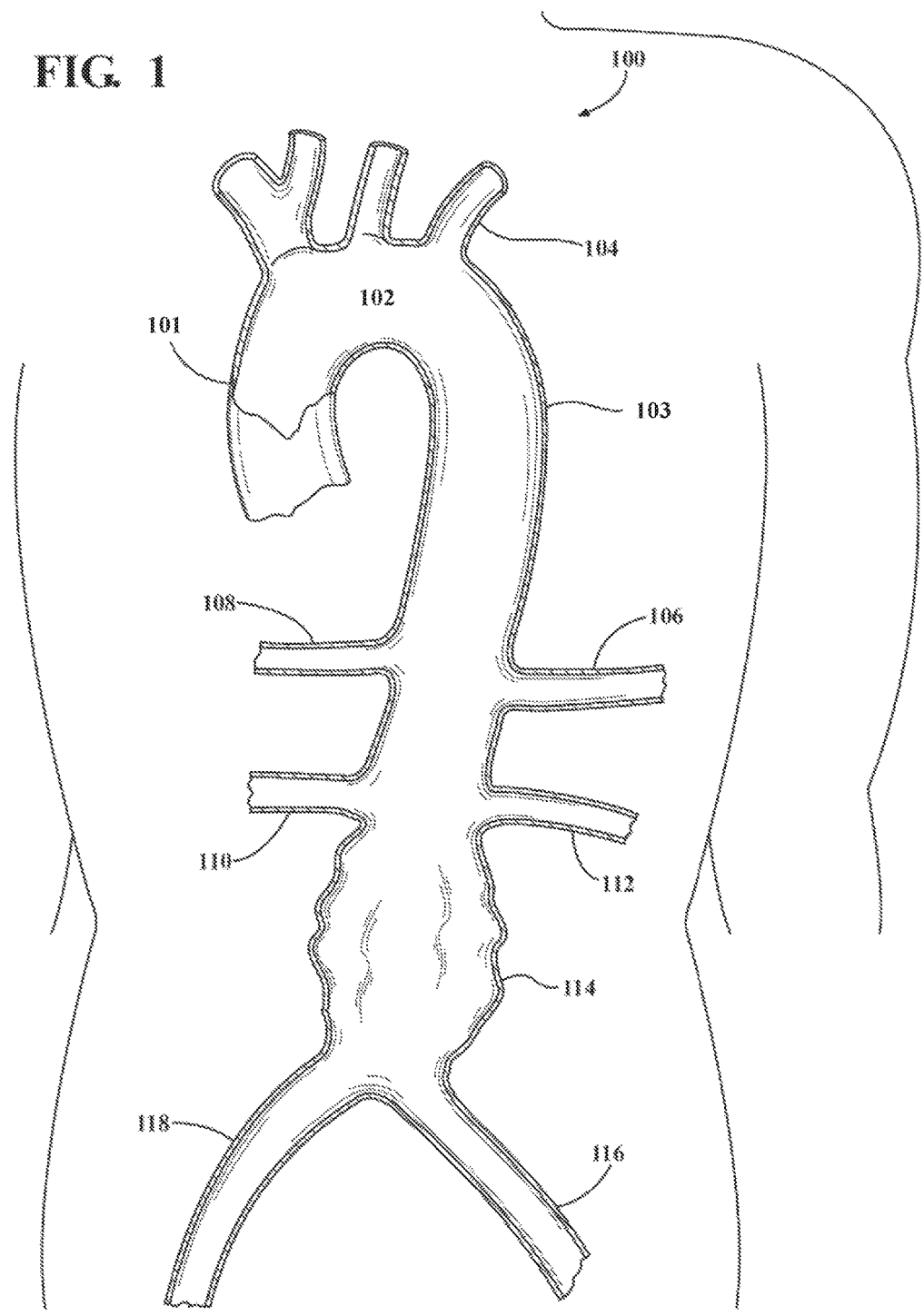
FIG. 1 is a cross-sectional representation of a human anatomy showing an aorta, left subclavian artery, celiac artery, superior mesenteric artery, two renal arteries and two iliac arteries.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

Devices, systems and methods of endoluminally delivering a branchable expandable implant in accordance with various embodiments are disclosed herein for treating disease of human vasculature. Although the description below and figures are illustrated in the context of treating the aorta 100, including the ascending aorta 101, aortic arch 102, and descending aorta 103, it should be appreciated that the present disclosure can be applied to treatment of other portions of the vasculature, including, for example, any disease where a larger vessel and one or more branch vessels are to be treated.

Figure 2:
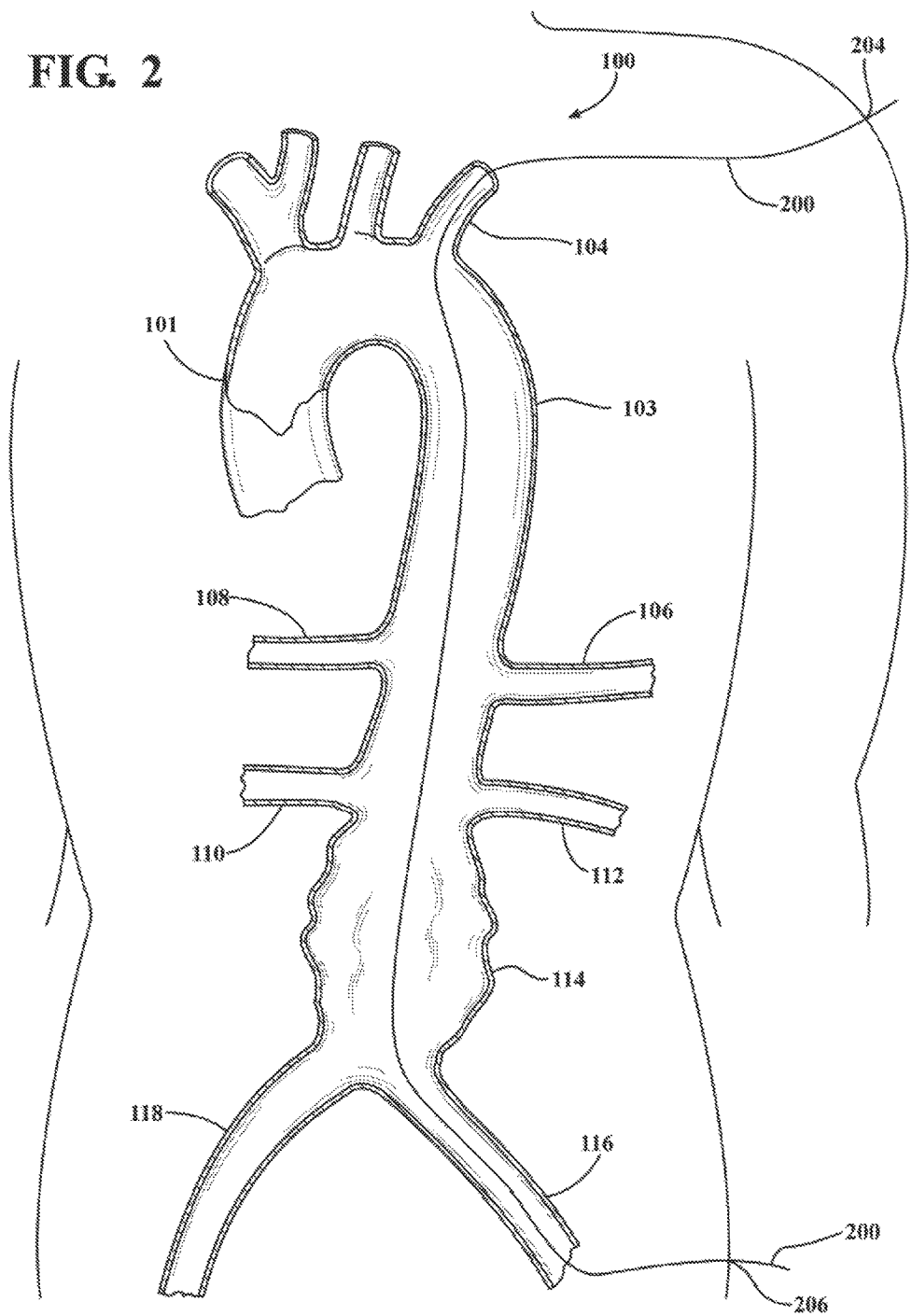
FIG. 2 is the cross-sectional representation of a human anatomy with a guidewire extending out of upper and lower access sites and transversing the left subclavian artery, the aorta and a single iliac artery.

In various embodiments, a method of endoluminally delivering a branchable expandable implant can include inserting a first guidewire into the vasculature through one of a first access site and second access site, through the vasculature to be treated, and out of the other of the first access site and second access site, such that the guidewire extends through the vasculature to be treated and opposite ends of the first guidewire extend outside of the body through respective access sites. As shown in FIG. 2, for example, a first guidewire 200 is inserted into the left subclavian artery (LSA) 104 through a first access site 204, routed through the descending aorta 103 and one of the iliac arteries 116 and 118, and out of the second access site 206, such that the first guidewire 200 extends through the aorta 100 and, more specifically, through the treatment site 114, and opposite ends of the first guidewire 200 extend outwardly from the body from respective access sites 204, 206.

Figure 4:
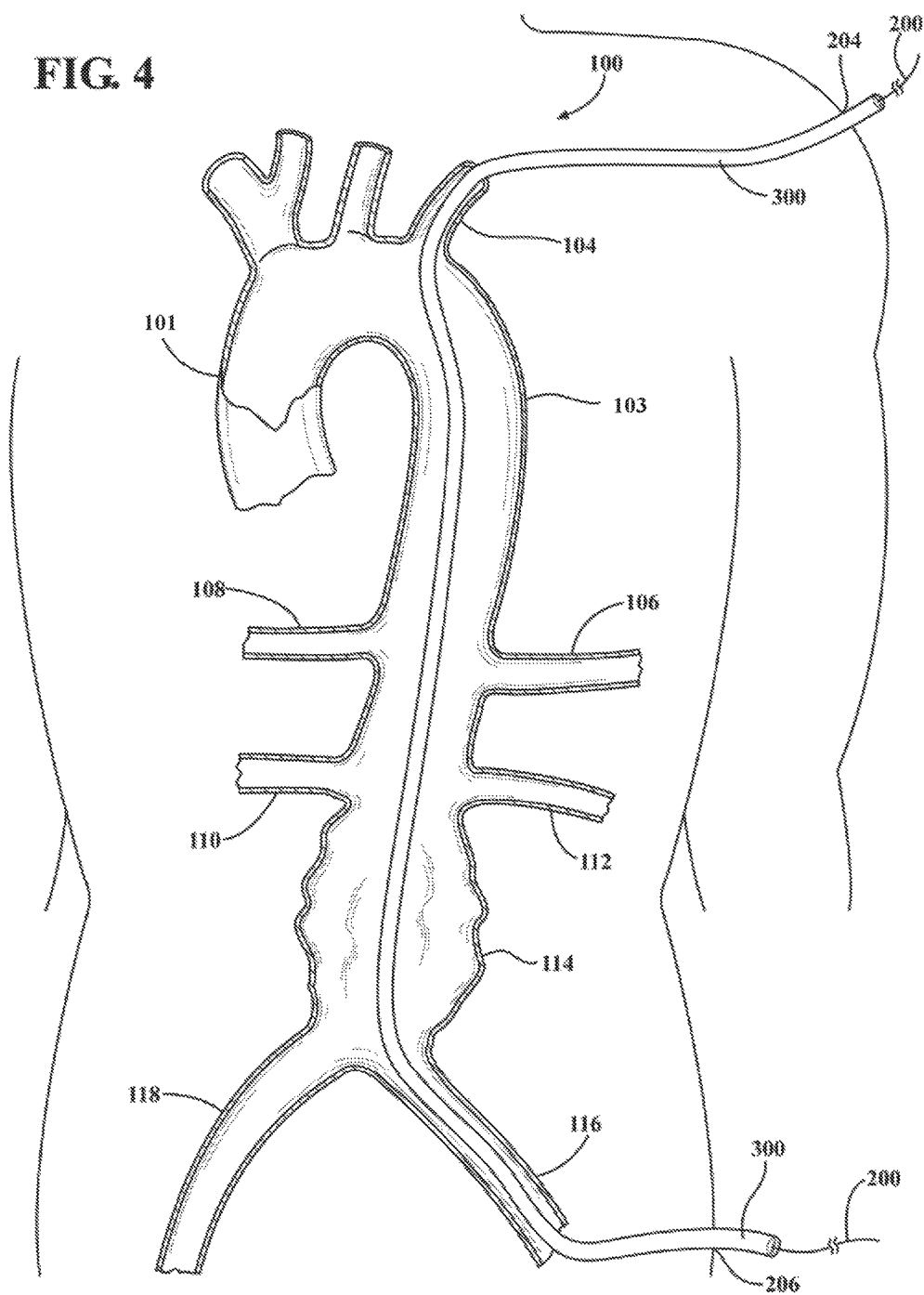
FIG. 4 is the cross-sectional representation of a human anatomy with a three lumen catheter and a guidewire extending out of upper and lower access sites and transversing the left subclavian artery, the aorta and a single iliac artery.

The method also includes inserting an end of the first guidewire into a leading end of an elongated delivery member, such as an introducer sheath or catheter, and inserting the leading end of the elongated delivery member into the vasculature along the first guidewire through one of the first and second access sites, and pushing the elongated delivery member along the first guidewire through the vasculature until the leading end exits the body through the other of the one of the first and second access sites. For example, as illustrated in FIG. 4, the first guidewire 200 is inserted into a leading end of a first catheter 300 and the first catheter 300 is passed along the first guidewire 200 and into the vasculature via the first access site 204. The first catheter 200 is pushed until the leading end of the first catheter 200 exits the iliac and/or femoral artery and the body through the second access site 206. Thus, the first guidewire 200 and first catheter 300 extend through the aorta and, more specifically, through the treatment site 114, and opposite ends of each of the first guidewire 200 and first catheter 300 extend outwardly from the body from respective access sites 204, 206.

Catheters, introducer sheaths, hubs, handles and other components usable in medical device delivery systems and methods disclosed herein can be constructed using any suitable medical grade material or combination of materials using any suitable manufacturing process or tooling. Suitable medical grade materials can include, for example, nylon, polyacrylamide, polycarbonate, polyethylene, polyformaldehyde, polymethylmethacrylate, polypropylene, polytetrafluoroethylene, expanded polytetrafluoroethylene, polytrifluorochlorethylene, polyvinylchloride, polyurethane, elastomeric organosilicon polymers, Pebax® polyether block amide, and metals such as stainless steels and nitinol. Catheters can also include a reinforcing member, such as a layer of metal braid.

Figure 5:
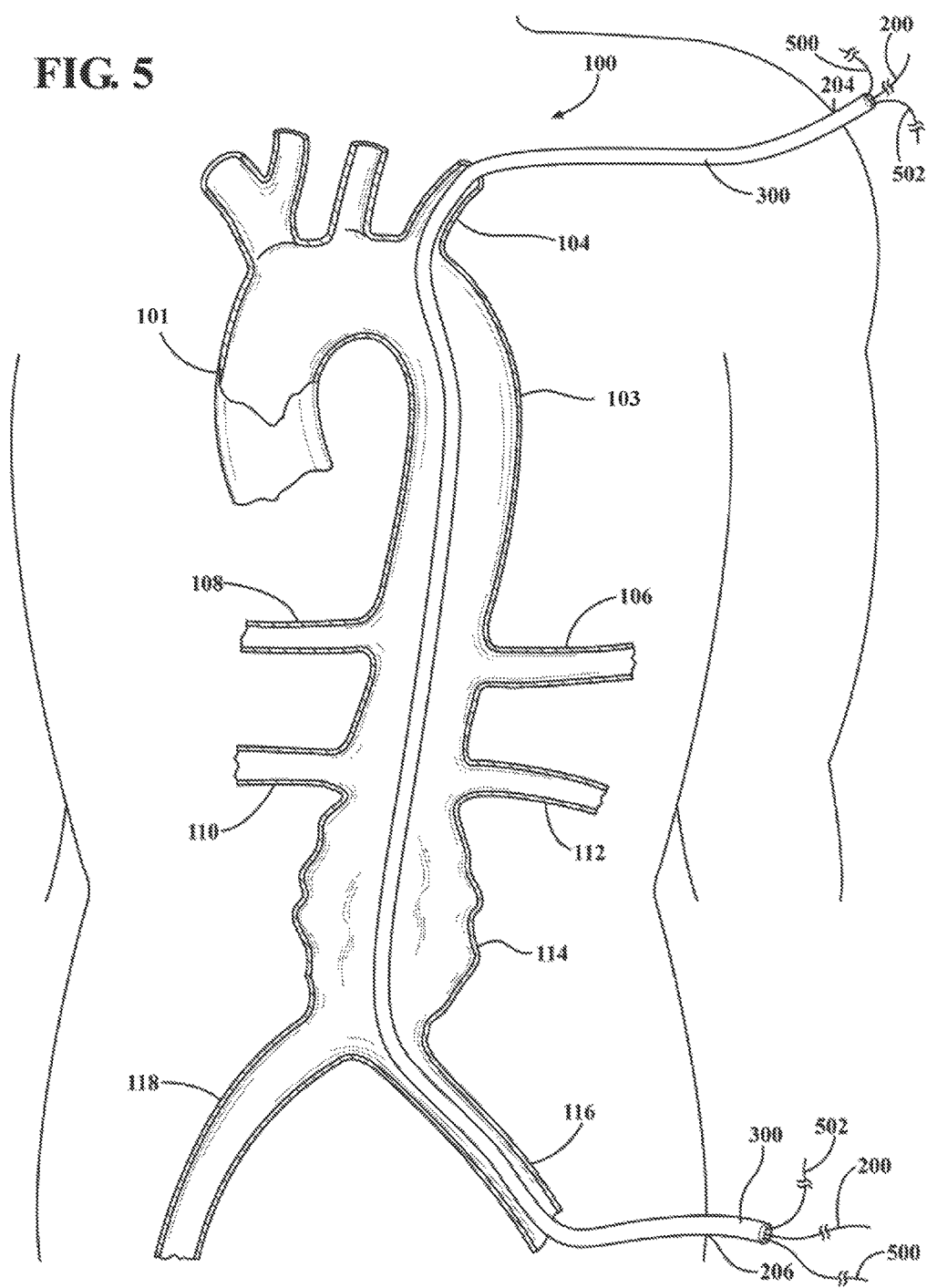
FIG. 5 is the cross-sectional representation of a human anatomy with a three lumen catheter with three guidewires extending out of upper and lower access sites and transversing the left subclavian artery, the aorta and a single iliac artery.

The method also includes inserting a second guidewire completely through the first catheter, such that opposite ends of the second guidewire extends outwardly from the body from respective access sites. As necessary, a third guidewire can be inserted completely through the first catheter, such that opposite ends of the third guidewire extends outwardly from the body from respective access sites. As shown in FIG. 5, for example, a second guidewire 500 and a third guidewire 502 are each routed completely through the first catheter 300 and, therefore, through the vasculature 100 and treatment site 114, such that opposite ends of each of the second 500 and third 502 guidewires extend outwardly from respective access sites 204, 206 via respective opposite ends of the first catheter 300.

Figure 3A:
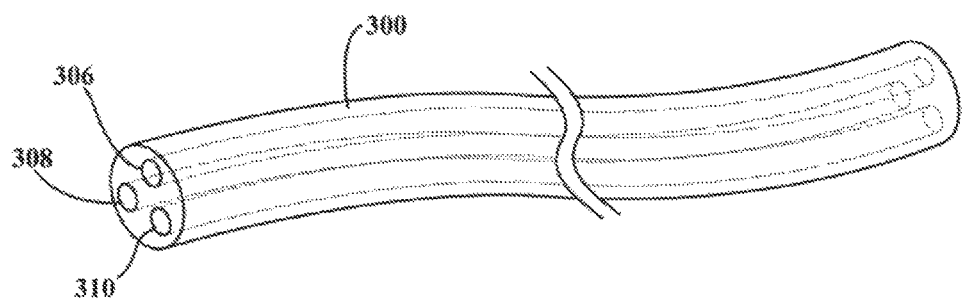
FIG. 3A through 3D are perspective views of a three lumen catheter having optional shaped lumens and a proximal tapered end.
Figure 3B:
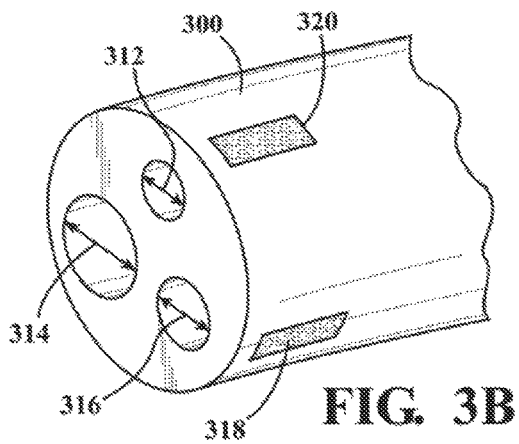
Figure 3C:
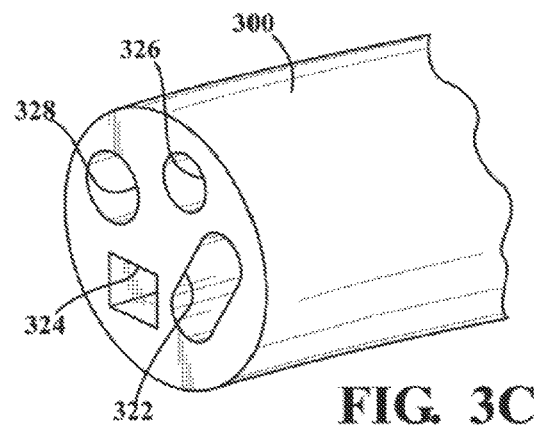
Figure 3D:
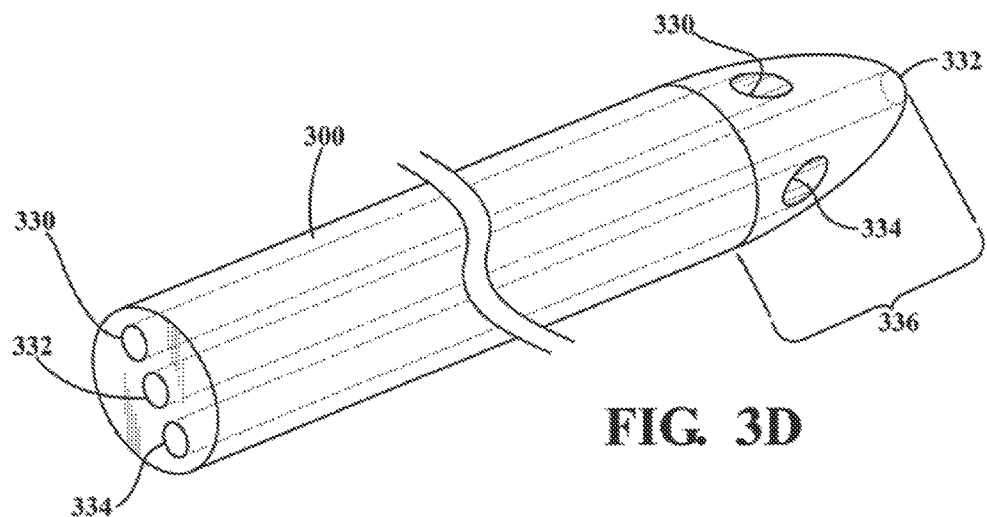

In various embodiments, a catheter having a plurality of lumens for managing a plurality of guidewires can be provided and used in methods disclosed herein. As shown in FIGS. 3A-3D, for example, the first catheter 300 can include first 306, second 308 and third 310 lumens for receiving the first 200, second 500 and third 502 guidewires, respectively, therethrough. The lumens can be provided in varying diameters, as illustrated at 312, 314, 316 in FIG. 3B. The lumens can also be provided in varying cross-sectional shapes, as illustrated at 322, 324, 326, 328 in FIG. 3C. Further, the lumens can be provided in cross section in a variety of orientations relative to each other. For example, as shown in FIG. 3D, the lumens 330, 332, 334 are shown arranged linearly in cross section. Still referring to FIG. 3D, the first catheter 300 can include a distal olive 336, wherein the lumens 330, 332, 334 in the first catheter 300 extend through the distal olive 336 to allow the guidewires to pass through both the catheter and the distal olive.

Referring back to FIG. 3B, the first catheter 300 can also include radiopaque markers 318, 320 to facilitate viewing on an x-ray fluoroscope during an implantation procedure. Any number, shape and location of radiopaque markers can be utilized as needed.

Delivery systems and methods disclosed herein are particularly suited for endoluminal delivery of branchable expandable implants for treating branched vasculature. Expandable implants can include, for example, stents, grafts, and stent grafts. Further, expandable implants can include one or more stent components 604 with one or more graft members disposed over and/or under the stent, which can dilate from a delivery configuration, through a range of larger intermediary configurations, and toward a deployed configuration engaged with vessel walls at a treatment site. However, and as discussed below, any suitable combination and configuration of stent component(s) and graft member(s) is within the scope of the present disclosure. For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly (caprolactones), poly(lactic/glycolic acid) polymers, poly (hydroxybutyrates) and poly(orthoesters).

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof. Any graft member which can be delivered by a catheter is in accordance with the present disclosure. Further detail of materials and general construction of stents, graft members and stent grafts are generally disclosed in U.S. Pat. Nos. 6,042,605; 6,361,637; and 6,520,986 all to Martin et al.

In various embodiments, a stent component and/or graft member can comprise a therapeutic coating. In these embodiments, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

Referring to FIG. 6A, for example, a branchable expandable implant 600 can be provided having opposite proximal 622 and distal 624 ends, a main lumen extending axially between the proximal 622 and distal 624 ends, and branch portals 606, 610, 614, 618 for receiving respective branch devices therethrough for directing a portion of blood flow from the main lumen to branch vessels. In various embodiments, the branch portals can be arranged in pairs 606, 614 and 610, 618 on opposite sides of a middle section 602 of the expandable implant 600. Other locations, arrangements or groupings of branch portals can be utilized depending on the vessel and branch vessels to be treated. Further, branch portals can face in the proximal direction, distal direction, radially outwardly facing, any angles relative to the main lumen axis, or any combination thereof.

Still referring to FIG. 6A, the expandable implant 600 can also include internal branch supports 608, 612, 616, 620, which are in fluid communication with respective branch portals 606, 610, 614, 618 and which provide support to and maintain orientation of branch devices extending therethrough. Further detail of materials and general construction of internal branch supports are generally disclosed in U.S. Pat. No. 6,645,242 to Quinn and in US 2011/0087318 to Daugherty et al.

Delivery systems and methods in accordance with various embodiments disclosed herein can utilize removable guidewires to preserve branch portals for guidewire cannulation therethrough subsequent to compacting the expandable implant toward a delivery configuration for endoluminal delivery to the treatment site. As shown in FIG. 6B, for example, a first removable guidewire tube 626 can be inserted through branch portals 606, 610 from each branch portal pair. Similarly, a second removable guidewire tube 628 can be inserted through the other branch portals 614, 618 from each branch portal pair. Opposite ends 630, 632 and 634, 636 of the first 626 and second 628 removable guidewire tubes extend axially beyond the proximal 622 and distal 624 ends of the expandable implant 600, respectively. Removable guidewire tube can comprise the same materials listed above for the catheter materials. Further details of materials and general construction of removable guidewire tubes are described in U.S. Pat. No. 8,273,115 to Hamer et al.

Figures 6C, 6D:
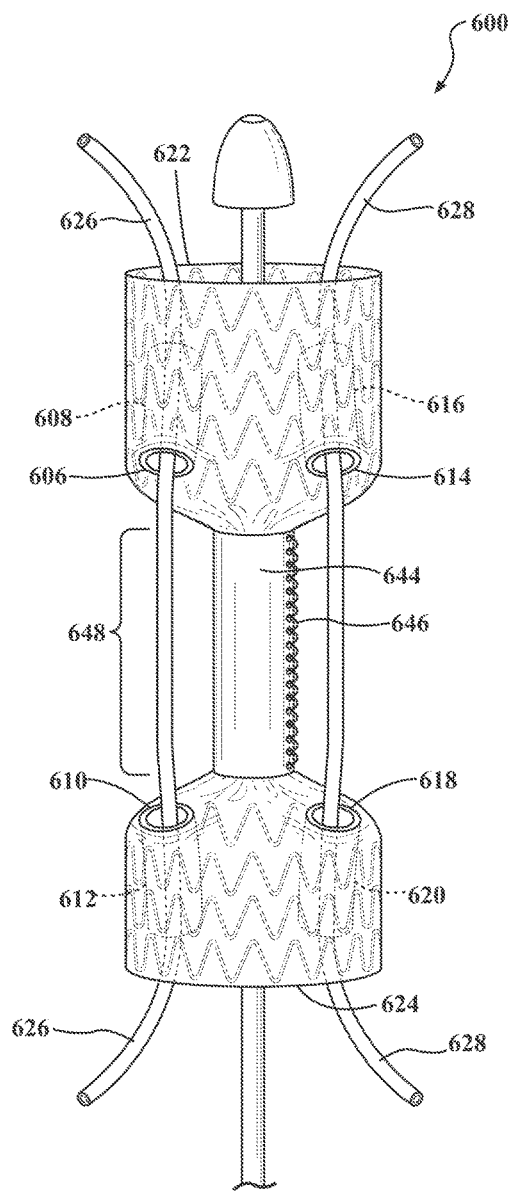
FIG. 6C is a perspective view of a stent graft having four side branch portals, two removable guidewire tubes. The mid-section of the stent graft is shown compressed onto a delivery catheter.
FIG. 6D is a perspective view of a stent graft having four side branch portals, two removable guidewire tubes. The stent graft is fully constrained in a compacted delivery state.

In various embodiments, a branchable vascular endoprosthetic device with one or more removable guidewire tubes extending through branch portals thereof can be radially compacted and retained on a delivery catheter in a delivery configuration for endoluminal delivery to the treatment site. For example, as shown in FIG. 6D, the expandable implant 600 is coupled to and supported on a delivery catheter 638 adjacent a distal end of the delivery catheter 638. A distal olive 640 is fixedly secured to distal end of the delivery catheter 638. A lumen 642 extends axially through the length of the delivery catheter 638 and the distal olive 640 to allow a guidewire to be fed therethrough. A primary constraining sleeve 680 extends over and releasably constrains the expandable implant 600 toward a compacted delivery configuration. An elongated first coupling member 652, such as a fiber or wire, stitches opposing edges or sides of the primary constraining sleeve together to releasably constrain the expandable implant 600. The primary constraining sleeve 680 can be opened by de-coupling the first coupling member 652 from the primary constraining sleeve 680. Further details of materials and general construction of constraining sleeves can be found in U.S. Pat. No. 6,352,561 to Leopold et al.

Opposite proximal 630, 634 and distal 632, 636 ends of each removable guidewire tube 626, 628 extend beyond respective opposite ends 682 and 684 of the primary constraining sleeve 680 to allow guidewires to be routed through the branch portals 606, 610, 614, 618 via the removable guidewire tubes 626, 628 even though the expandable implant is radially inwardly compressed toward or otherwise covered while in the delivery configuration by the primary constraining sleeve 680.

In various embodiments, one or more intermediate constraining sleeves can be utilized to releasably retain any portion or portions of a branchable vascular endoprosthetic device toward the delivery configuration or, alternatively, an intermediate configuration after opening or release of the primary constraining sleeve, wherein the intermediate configuration is larger than the delivery configuration and yet still smaller than a deployed configuration engaged with the vasculature. As illustrated in FIG. 6C, for example, a secondary constraining sleeve 644 extends over the middle portion 648 and releasably retains the middle portion 648 toward the delivery configuration after opening the primary sleeve. Alternatively, the secondary constraining sleeve can be sized to retain the middle portion toward an intermediate configuration which is larger than the delivery configuration and smaller then the deployed configuration. An elongated second coupling member 646 stitches opposing edges or sides of the secondary constraining sleeve 644 together to releasably constrain the middle portion 648 of the expandable implant 600.

By this arrangement, the expandable implant can be deployed in a staged sequence, wherein the primary constraining sleeve is opened first to allow the portions of the expandable implant that are not retained by the secondary sleeve to expand outwardly toward a deployed configuration engaged with the vessel walls. As illustrated in FIG. 6C, for example, proximal 622 and distal 624 ends of the expandable implant 600, which are not constrained by the secondary constraining sleeve 644 are allowed to expand toward the deployed configuration after opening the primary constraining sleeve.

Alternatively, a single coupling member may be utilized to stitch both the primary and secondary constraining sleeves. By this arrangement, the single coupling member can be decoupled from the primary and secondary constraining sleeves in sequence to render a staged deployment.

Alternatively, one or more secondary or intermediate constraining sleeves can be utilized releasably constrain one or more portions of the expandable implant after opening the primary constraining sleeve.

Figure 7:
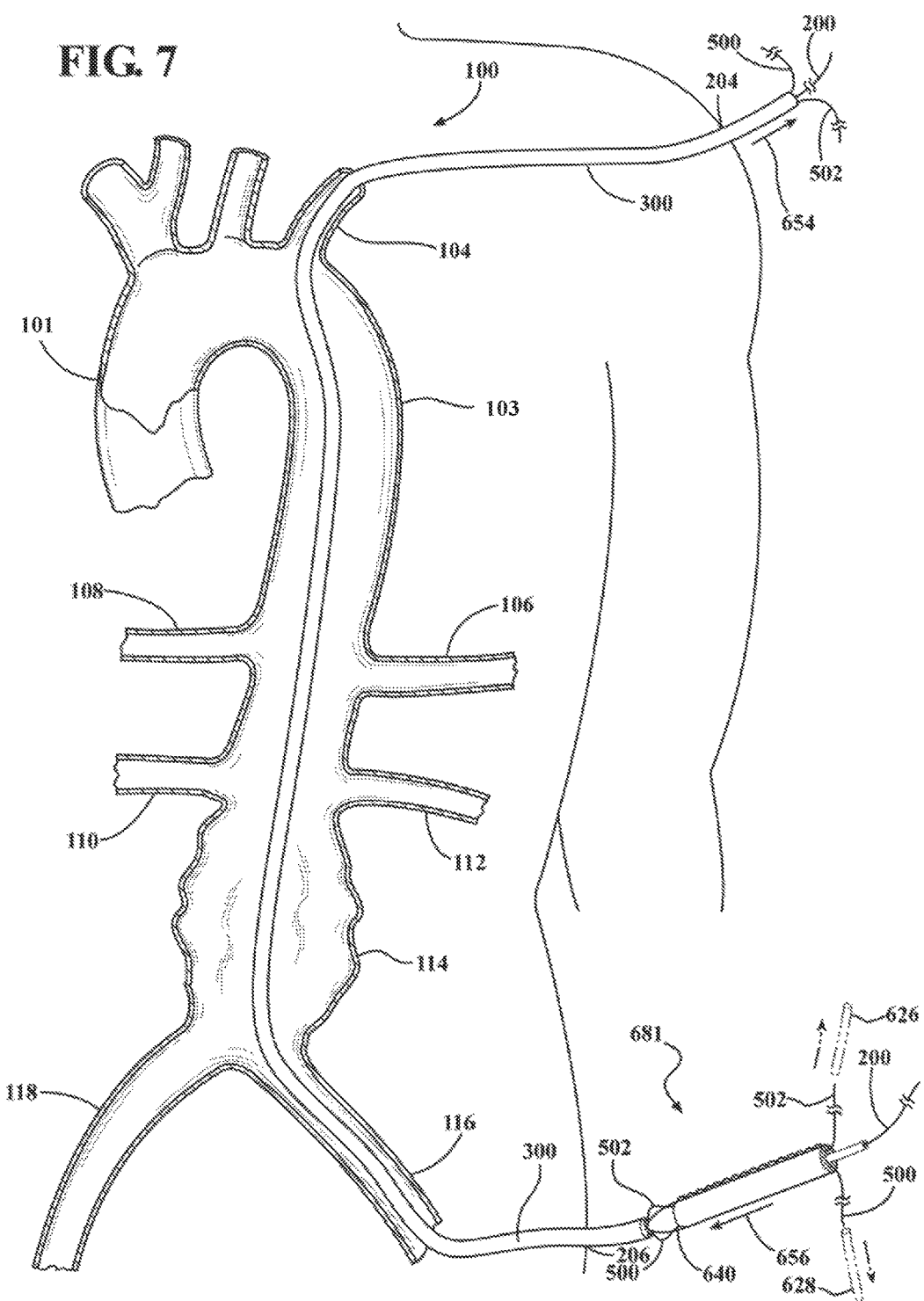
FIG. 7 is the cross-sectional representation of a human anatomy with a three lumen catheter with three guidewires extending out of upper and lower access sites and transversing the left subclavian artery, the aorta and a single iliac artery. A compacted stent graft is shown with the three guidewires routed through the compacted stent graft.

Referring to FIG. 7, the first guidewire 200 is inserted and routed through the distal olive 640 and delivery catheter 638 via the lumen 642. The second 500 and third 502 guidewires are routed through completely the first 626 and second 628 removable guidewire tubes and, therefore, beneath the primary constraining sleeve 600 and through the branch portals 606, 610 and 614, 618, respectively. With the second 500 and third 502 guidewires in place, the first 626 and second 628 removable guidewire tubes can be removed from the expandable implant 600, as indicated by the arrows in FIG. 7. Thus, a delivery catheter assembly 681 comprising the expandable implant 600 coupled to the delivery catheter 638 and releasably retained by the primary 680 and secondary 644 constraining sleeves is loaded onto the first 200, second 500 and third 502 guidewires for endoluminal delivery to the treatment site 114. The delivery catheter assembly 681 is pushed toward abutment or engagement with the first catheter 300. Abutment or engagement between the delivery catheter assembly 681 and the first catheter 300 can occur outside the access vessel, for example as shown in FIG. 7, or alternatively within an access sheath previously placed within the access vessel.

Figure 8:
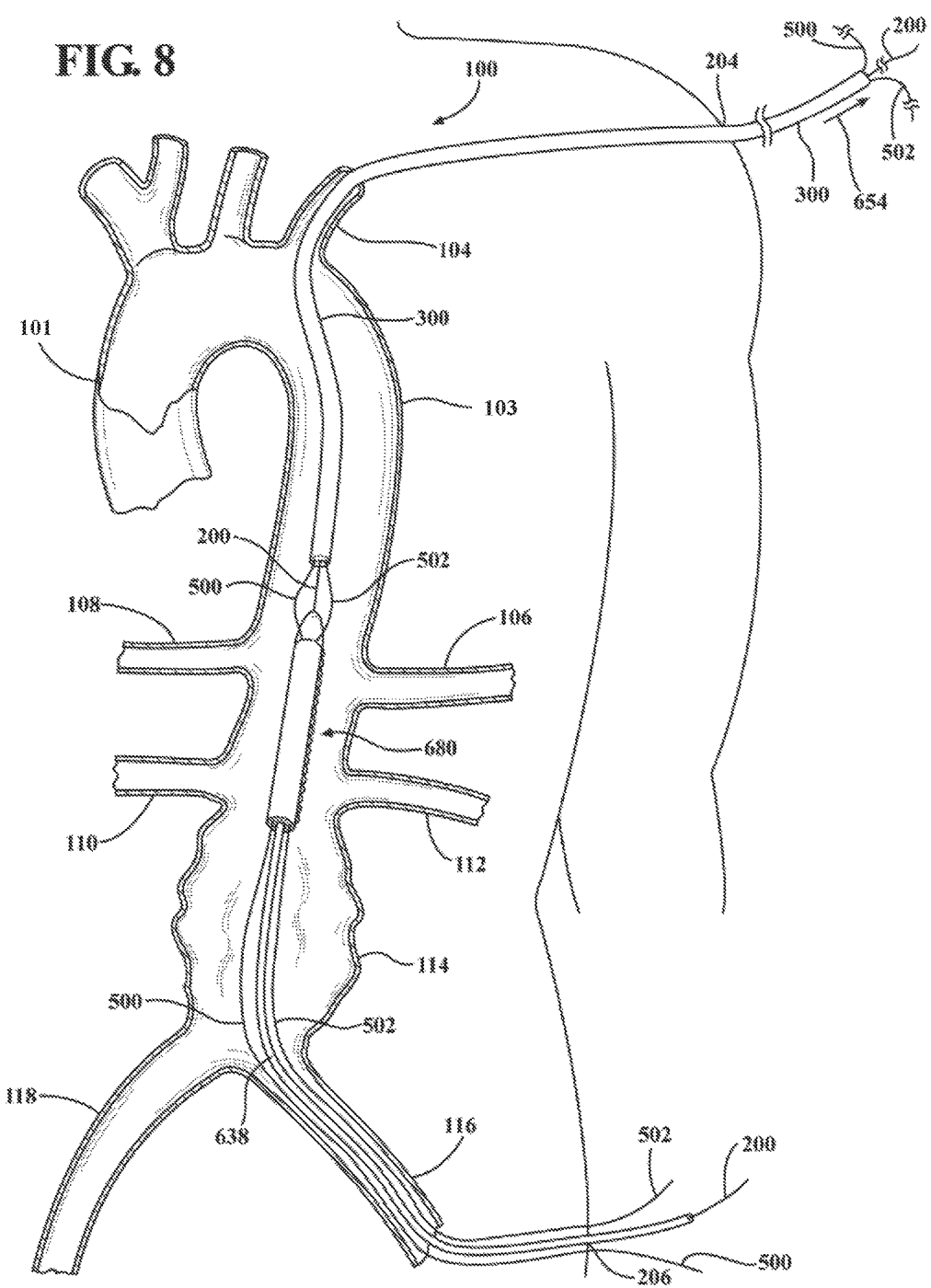
FIG. 8 is the cross-sectional representation of a human anatomy with a three lumen catheter with three guidewires extending out of upper and lower access sites and transversing the left subclavian artery, the aorta and a single iliac artery. A compacted stent graft is shown at the desired target site with the three guidewires routed through the compacted stent graft.

Referring to FIG. 8, the first catheter 300 and delivery catheter 638 are displaced together along and guided by the guidewires 200, 500, 502 proximally or in a direction indicated by arrow 654. The delivery catheter assembly 681 enters the vasculature 102 through the second access site 206 and displaced toward the treatment site 114. The first catheter 300 and delivery catheter 638 remain abutted as they are displaced along the guidewires 200, 500, 502. At the treatment site, the first catheter 300 and delivery catheter 638 can be pushed, pulled and rotated to position the expandable implant 600 to a desired location and orientation at the treatment site 114. Abutment of the first catheter 300 and delivery catheter 638 facilitates fine adjustments until the desired location and orientation at the treatment site is achieved. Conventional fluoroscopy techniques utilizing radiopaque markers on any one or multiple components of the delivery catheter assembly can be utilized to facilitate positioning of the expandable implant at the treatment site. For example, radiopaque markers can be located at or near the branch portals to facilitate orientation of the branch portals relative to the branch vessels 106, 108, 110, 112 to be treated.

Figure 9:
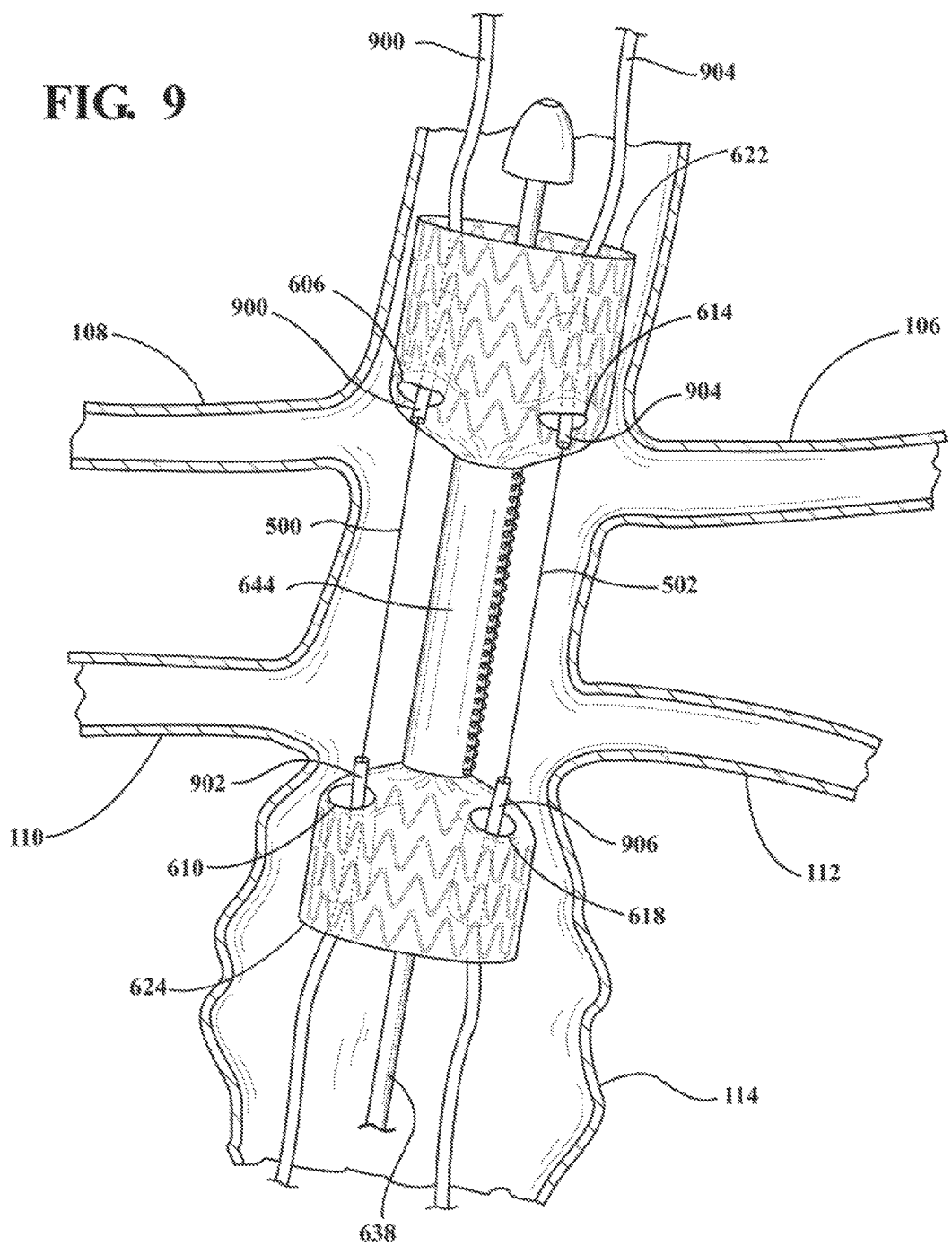
FIG. 9 is the cross-sectional representation of a human anatomy with a stent graft having a compacted mid-section along with expanded proximal and distal ends. Four guide catheters are shown routed over two guidewires.

After the desired position and orientation of the expandable implant is achieved, the primary constraining sleeve can be opened to allow portions of the expandable implant not constrained by secondary constraining sleeve to expand outwardly toward the deployed configuration either engaged with the vessel walls at the treatment site or at least fully expanded. As shown in FIG. 9, for example, opening the primary constraining sleeve 680 allows the proximal 622 and distal 624 ends of the expandable implant 600 to expand outwardly toward the deployed configuration. For the condition specifically shown in FIG. 9, where an aneurysmal sac is located below the branch vessels to be treated, the proximal end 622 engages the vessel wall above the branch vessels to be treated or, more particularly engages healthy vessel wall tissue above the celiac 106 and mesentery 108 arteries. The distal end 624 extends into the aneurysmal space at the treatment site 114.

The middle portion 648 between the proximal 622 and distal 624 ends of the expandable implant 600 remains constrained by the secondary constraining sleeve 644, thereby leaving a space between the vessel walls and the middle portion 648 to facilitate maneuvering of guidewire, catheters, devices and potentially other tools used to deliver, position and deploy branch devices in the branch portals and branch vessels.

Still referring to FIG. 9, guide or branch catheters 900, 902, 904, 906 are inserted into respective branch supports 608, 612, 616, 620 and through branch portals 606, 610, 614, 618 of the expandable implant 600 along the first 500 and second 502 guidewires, such that leading tips of each of the branch catheter assemblies 900, 902, 904, 906 extend into the space between the vessel walls and the middle portion 648. The first 500 and second 502 guidewires can then be removed from the body.

Figure 10:
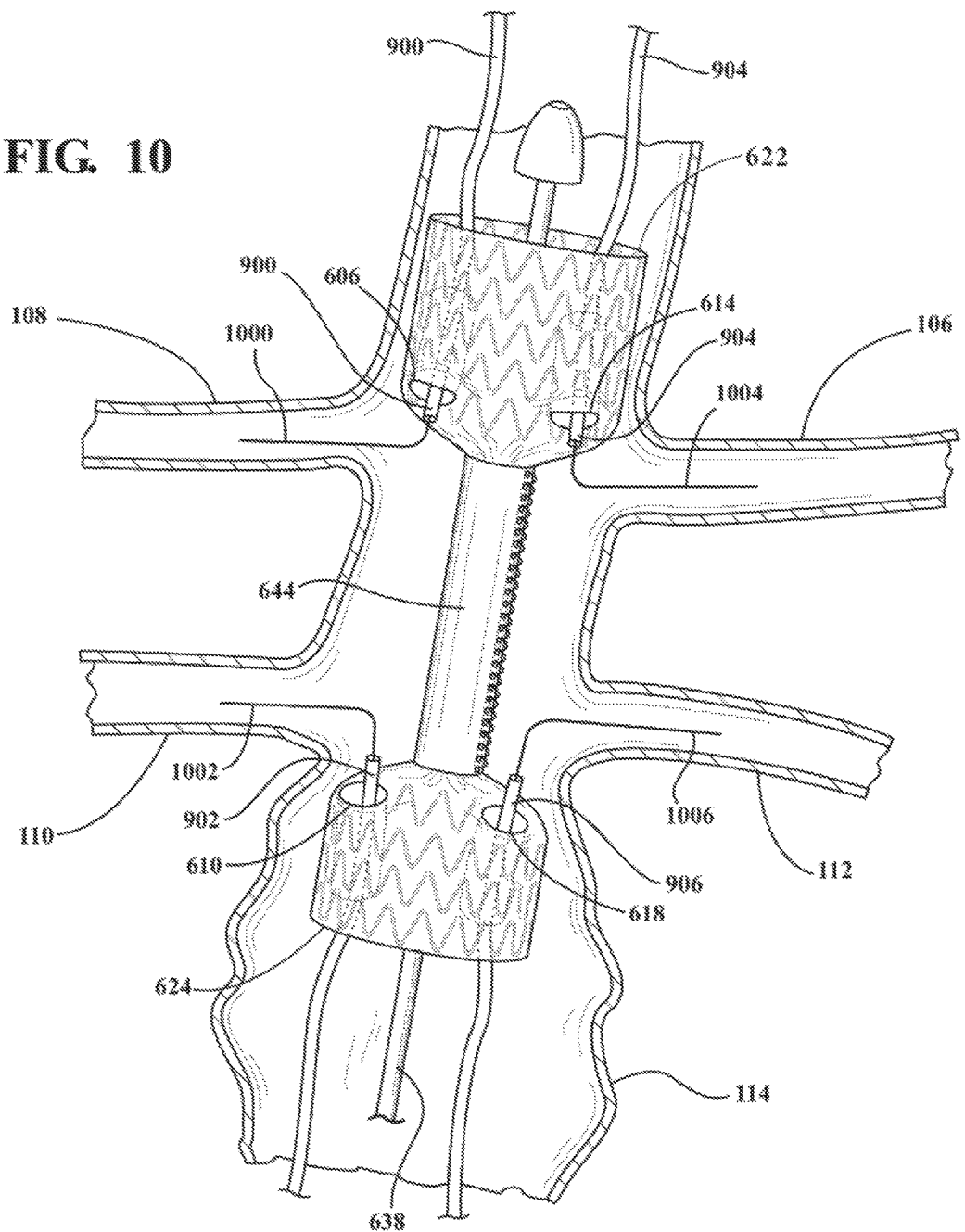
FIG. 10 is the cross-sectional representation of a human anatomy with a stent graft having a compacted mid-section along with expanded proximal and distal ends. Four side branch guidewires are shown routed through the four guide catheters and into four branch vessels.

Referring to FIG. 10, branch guidewires 1000, 1002, 1004, 1006 are inserted through lumens of respective branch catheters 900, 902, 904, 906 and introduced into the space between the vessel walls and the middle portion 648 of the expandable implant 600. The branch guidewires 1000, 1002, 1004, 1006 are then manipulated into branch vessels 106, 108, 110, 112.

Figure 11:
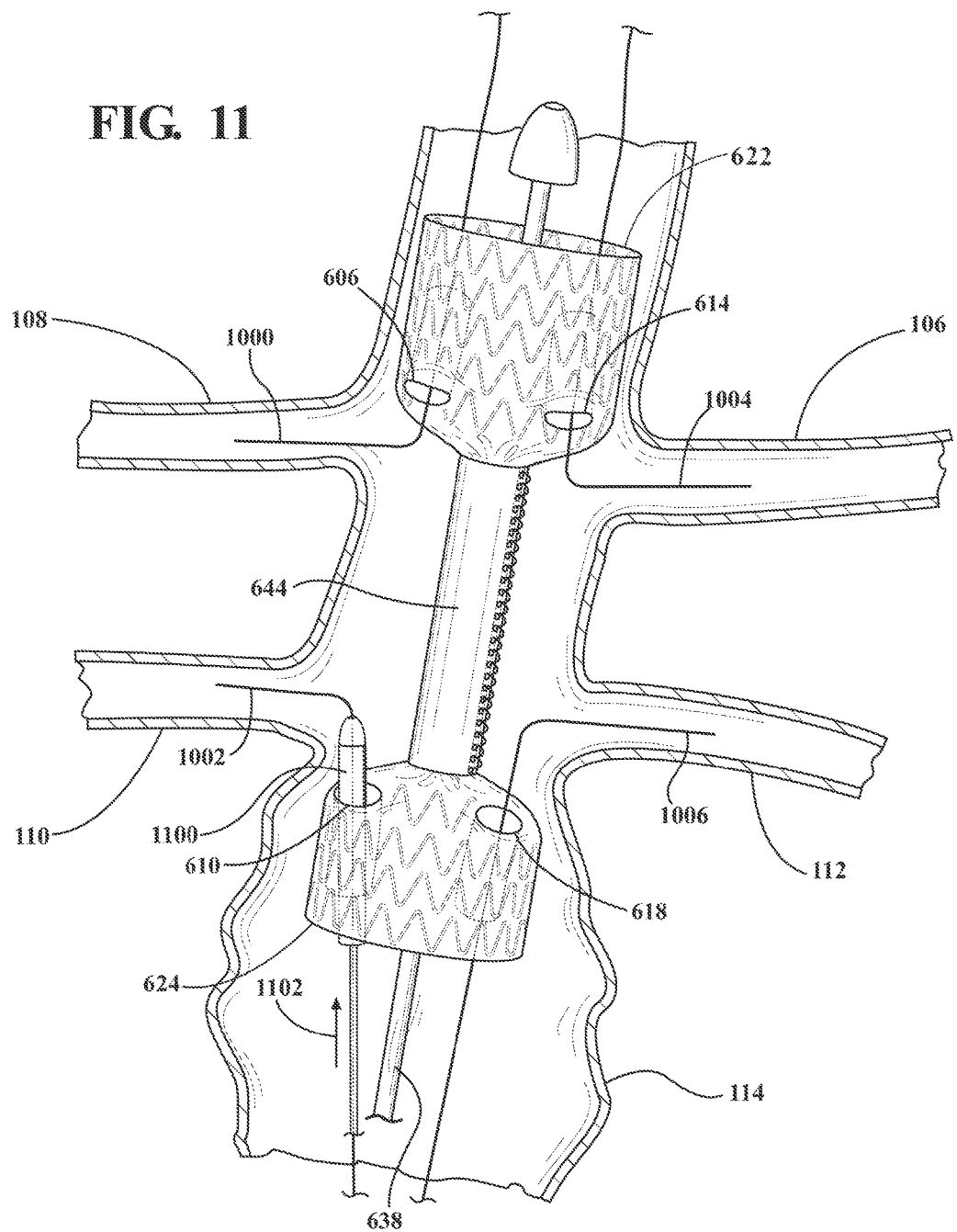
FIG. 11 is the cross-sectional representation of a human anatomy with a stent graft having a compacted mid-section along with expanded proximal and distal ends. Shown is a compacted side branch device being positioned into a branch vessel.

Referring to FIG. 11, the branch catheters 900, 902, 904, 906 are removed from the body, thereby leaving the branch guidewires 1000, 1002, 1004, 1006 in place extending through branch portals 606, 610, 614, 618 and into branch vessels 106, 108, 110, 112 to provide means for guiding 1102 branch catheter assemblies carrying branch devices 1100 into the branch vessels 106, 108, 110, 112.

Referring to FIG. 12, branch catheter assemblies (not shown) carrying branch devices constrained toward delivery configurations for endoluminal delivery, in a manner as described above with respect to the expandable implant, are delivered along branch guidewires 1000, 1002, 1004, 1006 and introduced into respective branch vessels 106, 108, 110, 112. The branch devices 1206, 1202, 1208, 1204, as illustrated in FIG. 12, are allowed to expand and engage the branch supports 608, 612, 616, 620 and branch vessels 108, 110, 106, 112, respectively.

For the specific condition illustrated in FIG. 12, a conventional aneurysmal excluder device can be deployed in the aneurysmal space at the treatment site 114 and coupled to the distal end 624 of the expandable implant 600, thereby completing exclusion of the aneurysmal space from normal blood flow. In situations where the aneurysm is located in other portions of the vaculature, for example, along the aorta between or among the branch vessels to be treated, for example between the superior mesenteric/celiac arteries 106, 108 and the renal arteries 110, 112, the proximal 622 and distal 624 ends of the expandable implant 600 can be deployed to engage healthy vessel tissue on opposite sides of the branch vessel grouping 106, 108, 110, 112. In either case or various other conditions, conventional extender stent graft devices can be deployed to extend from the proximal 622 and/or distal ends 624 of the expandable implant.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of treating a vessel and branch vessels extending therefrom, said method comprising:
  providing a catheter assembly comprising:
    a catheter;
    an expandable implant supported adjacent a leading end of the catheter, the expandable implant having opposite proximal and distal ends, a main blood flow lumen extending between the proximal and distal ends, a middle portion disposed between the proximal and distal ends, and at least one branch portal disposed between the middle portion and one of the proximal and distal ends;

a primary constraining sleeve that releasably constrains the expandable implant toward a delivery configuration for endoluminal delivery;

a secondary constraining sleeve that surrounds and releasably constrains the middle portion of the expandable implant after releasing the primary constraining sleeve; and a removable guidewire tube extending from the main blood flow lumen and through the at least one branch portal such that the removable guidewire tube is situated between the primary constraining sleeve and the secondary constraining sleeve with the expandable implant constrained in the delivery configuration;

routing a first guidewire through the removable guidewire tube with the expandable implant constrained in the delivery configuration;

endoluminally delivering the expandable implant to a desired location in a vessel;

releasing the primary constraining sleeve such that the proximal and distal ends and the at least one branch portal radially expand relative to the middle portion and the secondary constraining sleeve; and constraining the middle portion of the expandable implant with the secondary constraining sleeve to maintain a work space between the expandable implant and surrounding vessel walls to facilitate delivery of a branch device through the main blood flow lumen and the at least one branch portal and into a branch vessel to be treated.

2. The method as set forth in claim 1, wherein the removable guidewire tube extends from one of the proximal and distal ends of the expandable implant to allow insertion of the first guidewire therethrough while the expandable implant remains constrained by the primary constraining sleeve and prior to insertion of the catheter assembly in the vessel.

3. The method as set forth in claim 2 including placing a second guidewire through a lower access site, through an iliac artery, through an aortic artery, through a left subclavian artery and out of an upper access site, the second guidewire having proximal and distal ends exposed out of the upper and lower access sites respectively.

4. The method as set forth in claim 3 including supplying a multi-lumen catheter different from the catheter of the catheter assembly having proximal and distal ends with at least first and second independent thru lumens extending between the proximal and distal ends.

5. The method as set forth in claim 4 including placing the first lumen of the multi-lumen catheter over the second guide wire.

6. The method as set forth in claim 5 including advancing the multi-lumen catheter over the second guidewire through one of the lower and upper access sites such that the proximal and distal ends of the multi-lumen catheter are exposed out of the upper and lower access sites respectively.

7. The method as set forth in claim 6, wherein the proximal and distal ends of the second guidewire are exposed out of the proximal and distal ends of the multi-lumen catheter, respectively.

8. The method as set forth in claim 6 including advancing the first guidewire through the second lumen of the multi-lumen catheter.

9. The method as set forth in claim 8, wherein the proximal end and distal end of each of the first and second guidewires are exposed out of the proximal and distal ends of the multi-lumen catheter, respectively.

10. The method as set forth in claim 9 including:
removing the removable guidewire tube.

11. The method as set forth in claim 10 including:
advancing the expandable implant and the multi-lumen catheter along the first and second guidewires, so that the expandable implant is located at a desired treatment site; and
removing the multi-lumen catheter.

12. The method as set forth in claim 11 wherein the at least one branch portal includes a first side branch portal, the method further including advancing a first guide catheter having proximal and distal ends over the exposed proximal end of the first guidewire so that the distal end of the first guide catheter protrudes out of the first side branch portal of the expandable implant and the proximal end of the first guide catheter is exposed out of the upper access site.

13. The method as set forth in claim 12 wherein the at least one branch portal includes a second side branch portal, the method further including advancing a second guide catheter having proximal and distal ends over the exposed distal end of the second guidewire so that the proximal end of the second guide catheter protrudes out of the second side branch portal of the expandable implant and the distal end of the second guide catheter is exposed out of the lower access site.

14. The method as set forth in claim 13 including
removing the first guidewire; and
inserting a first side branch guidewire through the first guide catheter into a first side branch vessel.

15. The method as set forth in claim 14 including supplying a first side branch expandable implant in a compressed state on a first side branch delivery catheter, wherein the first side branch expandable implant is maintained in the compressed state by a first side branch external constraint.

16. The method as set forth in claim 15 including advancing the first side branch expandable implant along the first side branch guidewire into the first side branch vessel; and releasing the first side branch external constraint thereby allowing the first side branch expandable implant to expand into the first side branch vessel and into the first side branch portal.

17. The method as set forth in claim 14 including inserting a second side branch guidewire through the second guide catheter into a second side branch vessel.

18. The method as set forth in claim 17 including supplying a second side branch expandable implant in a compressed state on a second side branch delivery catheter, wherein the second side branch expandable implant is maintained in the compressed state by a second side branch external constraint.

19. The method as set forth in claim 18 including advancing the second side branch expandable implant along the second side branch guidewire into the second side branch vessel; and releasing the second side branch external constraint thereby allowing the second side branch expandable implant to expand into the second side branch vessel and into the second side branch portal.

20. The method as set forth in claim 19 including releasing the secondary constraining sleeve to allow the middle portion of the expandable implant to expand.

21. The method of claim 9 further comprising advancing a third guidewire through a third lumen of the multi-lumen catheter, the third guidewire having proximal and distal ends exposed out of the proximal and distal ends of the multi-lumen catheter.

22. The method of claim 21 further comprising advancing a third guide catheter having proximal and distal ends over the exposed proximal end of the third guidewire so that the distal end of the third guide catheter protrudes out of a third side branch portal of the expandable implant and the proximal end of the third guide catheter is exposed out of the upper access site.

23. The method of claim 22 further comprising advancing a fourth guide catheter having proximal and distal ends over the exposed distal end of the third guidewire so that the proximal end of the fourth guide catheter protrudes out of a fourth side branch portal of the expandable implant and the distal end of the fourth guide catheter is exposed out of the lower access site.

24. The method as set forth in claim 23 including:
removing the first and second guidewires; and
inserting third and fourth side branch guidewires through the third and fourth guide catheters and into third and fourth side branch vessels, respectively.

25. The method as set forth in claim 24 including:
supplying a third side branch expandable implant in a compressed state on a third side branch delivery catheter, wherein the third side branch expandable implant is maintained in the compressed state by a third side branch external constraint; and
advancing the third side branch expandable implant along the third side branch guidewire into the third side branch vessel; and releasing the third side branch external constraint thereby allowing the third side branch expandable implant to expand into the third side branch vessel and into the third side branch portal.

26. The method as set forth in claim 25 including:
supplying a fourth side branch expandable implant in a compressed state on a fourth side branch delivery catheter, wherein the fourth side branch expandable implant is maintained in the compressed state by a fourth side branch external constraint; and
advancing the fourth side branch expandable implant along the fourth side branch guidewire into the fourth side branch vessel; and releasing the fourth side branch external constraint thereby allowing the fourth side branch expandable implant to expand into the fourth side branch vessel and into the fourth side branch portal.

27. The method as set forth in claim 26 including releasing the secondary constraining sleeve to allow the middle portion of the expandable implant to expand.

28. A method of treating a vessel and branch vessels extending therefrom, said method comprising:
deploying opposite proximal and distal ends of an expandable implant from a primary constraining sleeve that releasably constrains the expandable implant toward a delivery configuration for endoluminal delivery such that the proximal and distal ends and at least one branch portal expand relative to a middle portion of the expandable implant, the middle portion is situated between the proximal and distal ends and is releasably constrained to a compacted state by a secondary constraining sleeve surrounding the middle portion of the expandable implant after the primary constraining sleeve is opened, wherein the expandable implant includes a main blood flow lumen extending between the proximal and distal ends, wherein the at least one branch portal is disposed between the middle portion and one of the proximal and distal ends, and wherein a guidewire is situated between the primary constraining sleeve and the secondary constraining sleeve when the expandable implant is constrained in the delivery configuration;
maintaining the middle portion of the expandable implant toward the compacted state with the secondary constraining sleeve to maintain a work space between the expandable implant and surrounding vessel walls;
delivering a branch device from the main blood flow lumen to a branch vessel to be treated via the at least one branch portal and expanding the branch device within the branch vessel; and
thereafter, releasing the secondary constraining sleeve such that the middle portion of the expandable implant expands relative to the proximal and distal ends and the at least one branch portal;
wherein the guidewire is routed through a removable guidewire tube extending from the main blood flow lumen and through the at least one branch portal such that the removable guidewire tube is situated between the primary constraining sleeve and the secondary constraining sleeve when the expandable implant is constrained in the delivery configuration.

29. The method as set forth in claim 28, wherein the at least one branch portal of the expandable implant includes a first pair of branch portals, the first pair of branch portals being disposed between the middle portion and the proximal end.

30. The method as set forth in claim 29, wherein the at least one branch portal of the expandable implant further includes a second pair of branch portals, the second pair of branch portals being disposed between the middle portion and the distal end.

31. A method of treating a vessel and branch vessels extending therefrom, said method comprising:
providing an expandable implant having opposite proximal and distal ends releasably constrained toward a delivery configuration for endoluminal delivery by a primary constraining sleeve, a main blood flow lumen extending between the proximal and distal ends, a middle portion releasably constrained by a secondary constraining sleeve disposed between the proximal and distal ends, a first branch portal disposed between the middle portion and the proximal end and a second branch portal disposed between the middle portion and the distal end;
endoluminally delivering the expandable implant in the delivery configuration along an auxiliary guidewire such that the first and second branch portals are advanced relative to the auxiliary guidewire, the auxiliary guidewire extending through the first and second branch portals such that the auxiliary guidewire exits the main blood flow lumen at the distal end of the expandable implant and is situated between the primary constraining sleeve and the secondary constraining sleeve when the expandable implant is constrained in the delivery configuration;
expanding the proximal and distal ends and the first and second branch portals by opening the primary constraining sleeve while maintaining the middle portion of the expandable implant toward a compacted state with the secondary constraining sleeve to maintain a work space between the expandable implant and surrounding vessel walls;
wherein the auxiliary guidewire is routed through a removable guidewire tube extending from the main blood flow lumen and through one of the first and second branch portals such that the removable guidewire tube is situated between the primary constraining sleeve and the secondary constraining sleeve when the expandable implant is constrained in the delivery configuration.

32. The method as set forth in claim 31, wherein opposite ends of the auxiliary guidewire are exposed and exit the vasculature from respective upper and lower access sites.

33. The method as set forth in claim 32 including advancing a first guide catheter having proximal and distal ends over one of the exposed opposite ends of the auxiliary guidewire so that the distal end of the first guide catheter protrudes out of the first branch portal of the expandable implant and the proximal end of the first guide catheter is exposed out of the upper access site.

34. The method as set forth in claim 33 including advancing a second guide catheter having proximal and distal ends over the other of the exposed opposite ends of the auxiliary guidewire so that the proximal end of the second guide catheter protrudes out of the second branch portal of the expandable implant and the distal end of the second guide catheter is exposed out of the lower access site.

35. The method as set forth in claim 34 including
removing the auxiliary guidewire; and
inserting a first side branch guidewire through the first guide catheter into a first side branch vessel.

36. The method as set forth in claim 35 including supplying a first side branch expandable implant in a compressed state on a first side branch delivery catheter, wherein the first side branch expandable implant is maintained in the compressed state by a first side branch external constraint.

37. The method as set forth in claim 36 including advancing the first side branch expandable implant along the first side branch guidewire into the first side branch vessel; and releasing the first side branch external constraint thereby allowing the first side branch expandable implant to expand into the first side branch vessel and into the first side branch portal.

38. The method as set forth in claim 37 including inserting a second side branch guidewire through the second guide catheter into a second side branch vessel.

39. The method as set forth in claim 38 including supplying a second side branch expandable implant in a compressed state on a second side branch delivery catheter, wherein the second side branch expandable implant is maintained in the compressed state by a second side branch external constraint.

40. The method as set forth in claim 39 including advancing the second side branch expandable implant along the second side branch guidewire into the second side branch vessel; and releasing the second side branch external constraint thereby allowing the second side branch expandable implant to expand into the second side branch vessel and into the second side branch portal.

41. The method as set forth in claim 40, the method further including releasing the secondary constraining sleeve such that the middle portion of the expandable implant is free to expand.

* * * * *